US012636732B2

(12) United States Patent
Renon et al.

(10) Patent No.: US 12,636,732 B2
(45) Date of Patent: May 26, 2026

(54) LASER EQUIPMENT FOR GOLD WORKSHOPS AND / OR DENTAL TECHNICIANS

(71) Applicant: OROTIG S.P.A, Castelonuovo del Garda (IT)

(72) Inventors: Alberto Renon, Castelonuovo del Garda (IT); Alberto Gagliano, Castelonuovo del Garda (IT)

(73) Assignee: OROTIG S.P.A., Castelnuovo del Garda (IT)

( * ) Notice: Subject to any disclaimer, the term of this patent is extended or adjusted under 35 U.S.C. 154(b) by 865 days.

(21) Appl. No.: 17/920,070

(22) PCT Filed: Apr. 19, 2021

(86) PCT No.: PCT/IB2021/053194
§ 371 (c)(1),
(2) Date: Oct. 20, 2022

(87) PCT Pub. No.: WO2021/214621
PCT Pub. Date: Oct. 28, 2021

(65) Prior Publication Data
US 2023/0084341 A1 Mar. 16, 2023

(30) Foreign Application Priority Data

Apr. 21, 2020 (IT) ........................ 102020000008485

(51) Int. Cl.
| | |
|---|---|
| *B23K 26/12* | (2014.01) |
| *A61L 9/20* | (2006.01) |
| *B23K 26/70* | (2014.01) |
| *B23K 37/006* | (2025.01) |

(52) U.S. Cl.
CPC .............. *B23K 26/127* (2013.01); *A61L 9/20* (2013.01); *B23K 26/702* (2015.10); *B23K 37/006* (2013.01); *A61L 2209/14* (2013.01)

(58) Field of Classification Search
CPC ....... A61C 13/20; A61L 2209/14; A61L 9/20; B23K 26/127; B23K 26/702; B23K 37/006
USPC ...................................... 219/121.86; 222/590
See application file for complete search history.

(56) References Cited

U.S. PATENT DOCUMENTS

| | | | |
|---|---|---|---|
| 4,400,270 A | 8/1983 | Hillman | |
| 7,862,728 B2 * | 1/2011 | Yencho | ................... C02F 1/325 |
| | | | 210/748.01 |

FOREIGN PATENT DOCUMENTS

| | | |
|---|---|---|
| CN | 202800634 U | 3/2013 |
| WO | 2011138753 A1 | 11/2011 |

OTHER PUBLICATIONS

Gagliano, WO 2011138753 A1 (Year: 2011).*

* cited by examiner

*Primary Examiner* — Vy T Nguyen
(74) *Attorney, Agent, or Firm* — Rivka Friedman

(57) ABSTRACT

A method is described for decontaminating room air by means of a tabletop apparatus (10) (or with dedicated stand) for the processing of metal costume jewelry/goldsmiths or dental prostheses through a LASER beam, wherein a source of UV and/or UV-C radiation irradiates a forced flow (F) of ambient air before it comes out of a casing of the apparatus.

17 Claims, 2 Drawing Sheets

LASER EQUIPMENT FOR GOLD WORKSHOPS AND / OR DENTAL TECHNICIANS

The invention relates to a laser apparatus, e.g. a tabletop apparatus or a portable apparatus and/or with a dedicated stand, for goldsmith and/or dental laboratories; in particular, a welding and/or marking and/or cutting machine for processing metal jewelry or dental prostheses or goldsmith artifacts by LASER. The invention also relates to a method for decontaminating ambient air by means of the apparatus in use.

Known laser welding devices of the above type are shown, for example, in PCT/IB2011/051990.

The year 2020 will undoubtedly be remembered only for the coronavirus and its victims. The resulting worldwide health chaos has forced populations to wear face masks for extended periods of time and take safety measures to prevent infection, especially in workplaces. This is especially true where there is a lot of laser equipment placed in arrays and/or in contiguous environments where the limited air volume is shared by many operators. Facing this new scenario of social coexistence, it is necessary to solve the problem of combining the need to keep the productive economic system alive with personal safety.

Solving or mitigating the above problem is the primary object of the invention, which is defined in the appended claims, wherein the dependent ones claims define advantageous variants.

A laser apparatus is proposed for processing metal costume jewelry/jewelry equipped with a LASER beam generator to process the object. The apparatus comprises an outer casing that delimits a processing chamber inside which the laser acts on the workpiece. The processing chamber may be closed, or partially closed, and is configured to allow access to the hands so as to load the workpiece. The processing under the laser may be done manually or by means of a device for automatically moving the workpiece inside the chamber; the loading of the workpiece inside the processing chamber is always manual. The device preferably comprises a microscope with which an operator can arrange and weld objects inside the chamber while observing where the laser acts, called the "working zone"; and/or a camera to film the working zone and a display to visualize the working zone enlarged; and/or a transparent inspection window or opening in the casing. Through the window or opening the operator can directly see the working zone, so it facilitates the positioning of the objects to be processed under the laser.

If the processing chamber is partially closed the casing preferably has an opening for the access to the processing chamber that extends, in use, at one side of the apparatus. and the transparent window is placed adjacent to the top edge of the opening. Thus the line of sight is directed toward the working zone while being in a comfortable position for the operator.

The device also comprises a fan or means to create a forced airflow coming out of the casing, a UV and/or UV-C (germicidal UV) radiation source preferably also assisted by a filter (e.g. of EPA type) to irradiate the airflow before it leaves the casing.

For the positioning of the radiation source, it is possible, for example, to take advantage of pre-existing paths or airflows through the Laser device, with low impact on the re-design.

One or more radiation sources may be integrated into the casing.

A or each source of radiation may be a UV and/or UV-C lamp or a led diode with light emitted at UV and/or UV-C frequency preferably also assisted by a filter (also of HEPA type).

Each radiation source may be mounted inside the casing or on the exterior surface of the casing.

The advantage is to exploit the apparatus as a system for decontaminating the air present in the workplace, in particular by exploiting the means of air movement already present in the apparatus. In fact, the apparatus ordinarily comprises a system of fans that serve, for example, to suck air either from the welding chamber, or to suck or push air from or towards electronic boards or components present inside the apparatus. The cooling system of the LASER is by circulating water. One or more fans create a flow of air that is passed through a radiator to cool the cooling water and/or even just a blower to suck in air.

A UV laser lamp or diode, especially UV-C, results in a marked knockdown (even over 90%) of viruses (H1N1), influenza A viruses, including Covid 19.

It is preferable and advantageous to optimize the apparatus by means of the operating logic, e.g. performed by means of an electronic processor 1000 (see FIG. 2), illustrated below.

Since the sterilized airflow is the same as that which cools the internal components, a higher air flow-rate is required when the apparatus is working and dissipating heat. The number of UV and/or UV-C sources (e.g., 56 in FIG. 3 and 1010 in FIG. 4) installed in the apparatus being the same, the decontamination efficiency drops with higher air flow-rates because the air stays less time in front of the UV and/or UV-C source. In this circumstance, one or more UV and/or UV-C sources may be partialized to save energy or additional UV and/or UV-C sources may be turned on to maintain a desired sterilization efficiency.

When the apparatus is switched on but the LASER source is not active, a sufficient amount of air is circulated through the apparatus to cool the electrical and electronic parts and to achieve continuous sanitization of the air taken from the working environment and returned filtered and sanitized to the environment itself. Another mode is one during prolonged inactivity (e.g. at lunch break or overnight) of the apparatus, which, however, remains always on. In this mode energy consumption can be reduced and the volume of air to be recycled in the working environment can be optimized. In particular, a series of air packets with a determined flow-rate or volume may be emitted cyclically from the apparatus. By subjecting still air to the radiation of the sanitizing source for a longer period of time, the air is decontaminated more effectively.

Preferably, the processor controls the flow-rate of the forced airflow by reading a signal emitted by a flow-meter or debimeter, so as to measure the flow-rate of the forced airflow and adjust a generator of the forced airflow so that the measured flow-rate equals a predetermined value.

Another aspect of the invention relates to a method for decontaminating ambient air by means of an aforementioned apparatus, particularly a tabletop apparatus or an apparatus with a dedicated stand, for processing metal costume jewelry/jewelry or dental prostheses by means of a LASER beam, wherein a UV and/or UV-C radiation source irradiates a forced flow of ambient air before it comes out of a casing of the apparatus.

The forced flow of ambient air entering the apparatus, sucked in by said fan or means for creating the flow, is potentially a carrier for viral particles. The forced flow of ambient air exiting the apparatus pushed by said fan or means for creating the flow is sanitized by the UV and/or UV-C radiation source mounted on board the apparatus. In particular, the forced airflow constitutes the air of a cooling circuit for internal components of the apparatus.

As variants of the method:

during operation of the LASER source (and in particular: only in this circumstance) the UV and/or UV-C radiation source is partialized; and/or during the operation of the LASER source (and in particular: only in this circumstance) an additional UV and/or UV-C radiation source, which for example was previously partialized, is activated or the effect of such additional UV and/or UV-C radiation source is increased; and/or during the inactivity of the LASER source (and in particular: only in this circumstance) the forced airflow is cyclically interrupted for a preset time; and/or the flow-rate of the forced airflow is measured and a forced airflow generator is regulated so that the measured flow-rate equals a preset value.

The advantages of the invention will be clearer from the following description of a preferred embodiment of the apparatus, reference being made to the accompanying drawing in which FIG. 1 shows a three-dimensional view of a LASER welding machine;

Figure 1:
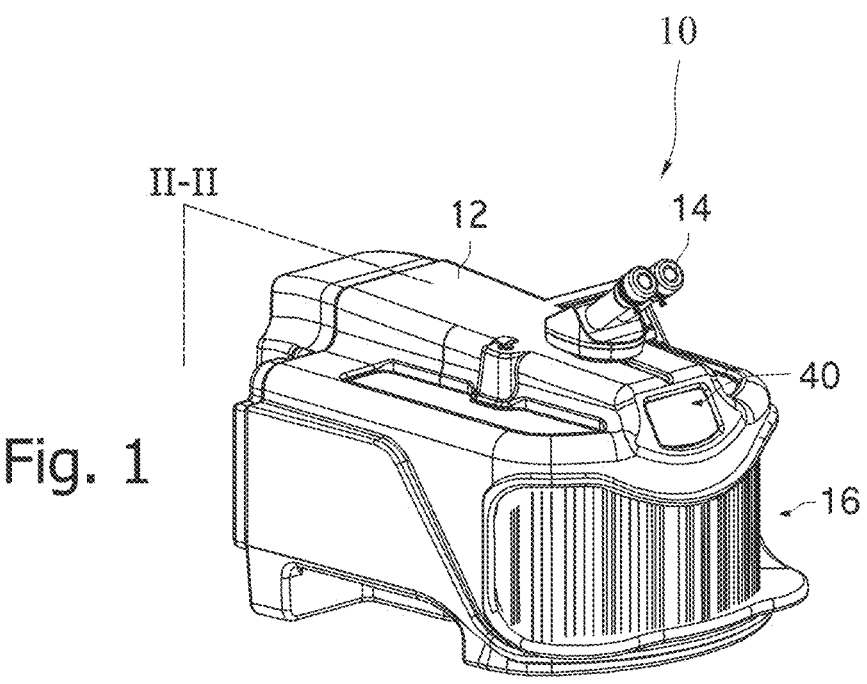

In the figures equal numbers indicate equal or conceptually similar parts, and the welding machine is described as in use. A welding machine 10 is illustrated herein as an example of an apparatus according to the invention. The welding machine 10 comprises a hollow outer casing 12 that internally delimits a cavity 20 in which an object can be processed by a laser 18 in a zone W. The cavity 20 is accessible to an operator's hands via a front opening 16 (optionally closed by a curtain) and observable via a microscope 14 mounted on the casing 12.

Figure 2:
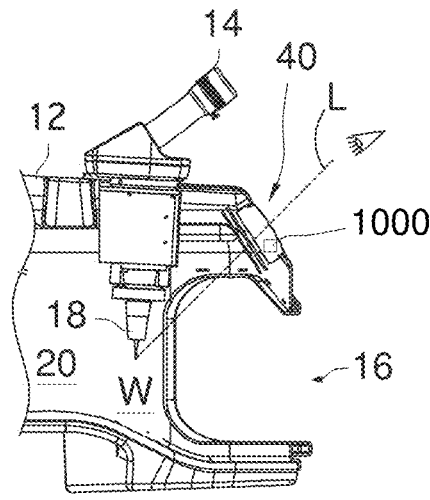
FIG. 2 shows a cross-sectional view according to the vertical median plane II-II of FIG. 1.

Above the opening 16, integrated into the casing 12, is an optional transparent inspection window 40 (see FIG. 2) for the zone W. The window 40 preferably comprises, from the outside in, a sequence of a magnifying glass 46, a protective filter to shield from laser radiation, and another optional shielding filter. A straight observation line L indicates the direct, straight optical path for observing the zone W from the window 40.

Figures 3, 4:
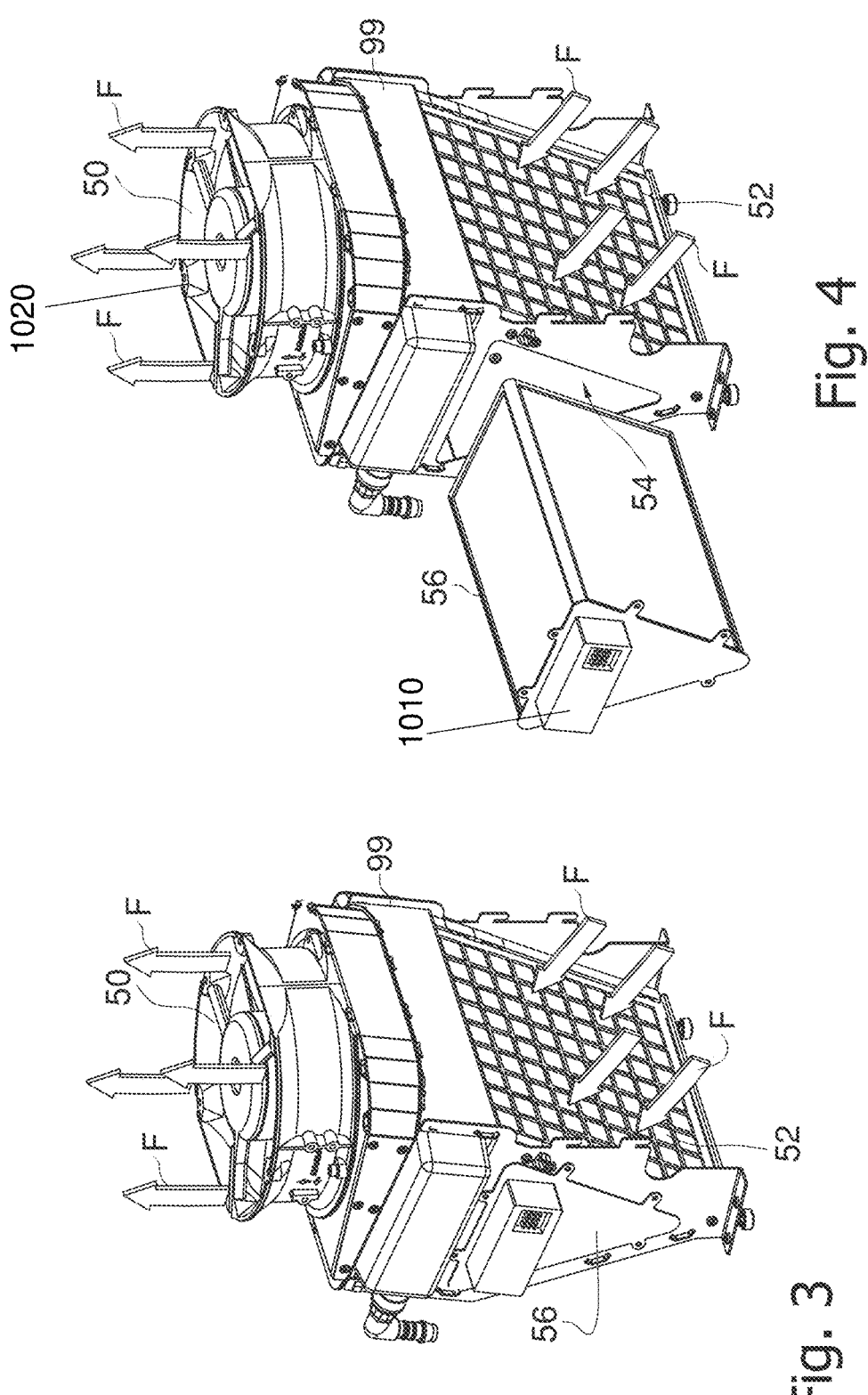
FIG. 3 shows part of a cooling circuit as assembled.
FIG. 4 shows the part of FIG. 3 as disassembled.

FIGS. 3 and 4 show a decontaminating device applicable to the welding machine 10, or in general to a portable device for processing metal jewelry through a LASER.

A fan 50 induces a forced airflow F (indicated by arrows) that passes through a grid and/or filter (e.g. of HEPA type) 52, enters a compartment 54 and exits the welding machine 10 pushed by the fan 50.

The compartment 54 is e.g. delimited by the walls of internal components of the welding machine 10. The grid and/or pre-filter 52 may belong to an (optional) radiator assembly 99 for cooling circulating cooling water for internal components of the welding machine 10. A source 56 of UV and/or UV-C radiation, such as a lamp, is installed in the compartment 54 to irradiate the airflow F before it exits the casing of the welding machine 10.

The air F is taken in a known manner from the environment, and during the ordinary circulation of air F inside the casing 12 to cool the welding machine 10, the air F is also decontaminated by the source 56 and preferably filtered before being released into the environment. Thus, people working around the welding machine 10 enjoy a safer environment. The sources 56 inside the welding machine 10 may also be more than one.

Preferably, the flow-rate of the airflow F, which is measured by a flow meter or an air-flow sensor 1020, is regulated by controlling the speed of the fan 50 through a processor (not shown). The processor is, for example, programmed to partialize the source 56 during the operation of the LASER source to save energy, or activate an additional UV and/or UV-C radiation source, previously inactive, to increase decontamination efficiency.

For example, the processor is programmed in such a way that, during the inactivity of the LASER source, the forced airflow F is cyclically interrupted for a predetermined time, in order to let the air F remain longer in front of the source 56 (inside the compartment 54).

The invention claimed is:

1. An apparatus for manual processing of metal costume jewelry and/or dental prostheses through a LASER, comprising:

a casing delimiting a closed or partially closed processing chamber which is configured to allow access to an operator's hands to load a workpiece to be processed, a LASER source configured to send a LASER beam into the processing chamber, a fan or means for creating a forced air flow coming out of the casing, a source of UV and/or UV-C radiation for irradiating the forced air flow before the forced air flow comes out of the casing.

2. The apparatus according to claim 1, comprising a filter to filter said forced air flow before the forced air flow comes out of the casing.

3. The apparatus according to claim 2, wherein said filter is a HEPA filter.

4. The apparatus according to claim 2, comprising an electronic processor programmed to partialize one or more UV and/or UV-C sources mounted inside the casing to save energy or switch on additional UV and/or UV-C sources mounted inside the casing to maintain decontamination.

5. The apparatus according to claim 4, comprising a flow meter or an air-flow sensor to measure a flow-rate of the forced air flow, and an electronic processor programmed to control the flow-rate of the forced air flow by reading a signal emitted by the flow meter or air-flow sensor so that the measured flow-rate is set equal to a predetermined value.

6. The apparatus according to claim 1, comprising an electronic processor programmed to partialize one or more UV and/or UV-C sources mounted inside the casing to save energy or switch on additional UV and/or UV-C sources mounted inside the casing to maintain decontamination.

7. The apparatus according to claim 6, comprising a flow meter or an air-flow sensor to measure a flow-rate of the forced air flow, and an electronic processor programmed to control the flow-rate of the forced air flow by reading a signal emitted by the flow meter or air-flow sensor so that the measured flow-rate is set equal to a predetermined value.

8. A method for decontaminating room air by means of an apparatus for manual processing of metal costume jewelry/ goldsmiths or dental prostheses through a LASER beam, wherein a source of UV and/or UV-C radiation radiates a forced air flow of ambient air before the forced air flow comes out of a casing of the apparatus.

9. The method according to claim 8, wherein the forced air flow constitutes air of a cooling circuit for internal components of the apparatus.

10. The method according to claim 9, wherein the source of UV and/or UV-C radiation is partialized during an operation of a LASER source.

11. The method according to claim 9, wherein during an inactivity of a LASER source, the forced air flow is cyclically interrupted for a predetermined time.

12. The method according to claim 9, wherein a flow-rate of the forced air flow is measured and a forced air flow generator is regulated so that the measured flow-rate is equal to a predetermined value.

13. The method according to claim 8, wherein the source of UV and/or UV-C radiation is partialized during an operation of a LASER source.

14. The method according to claim 13, wherein during the operation of the LASER source, an additional source of UV and/or UV-C radiation is activated or increased.

15. The method according to claim 8, wherein during an operation of a LASER source, an additional source of UV and/or UV-C radiation is activated or increased.

16. The method according to claim 8, wherein during an inactivity of a LASER source, the forced air flow is cyclically interrupted for a predetermined time.

17. The method according to claim 8, wherein a flow-rate of the forced air flow is measured and a forced air flow generator is regulated so that the measured flow-rate is equal to a predetermined value.

* * * * *